US00PP21580P3

(12) United States Plant Patent
Navarro et al.

(10) Patent No.: US PP21,580 P3
(45) Date of Patent: Dec. 21, 2010

(54) MANDARIN ORANGE TREE NAMED 'GARBI'

(50) Latin Name: *Citrus hydrida*
Varietal Denomination: Garbi

(75) Inventors: Luis Navarro, Valencia (ES); José Juárez, Valencia (ES); Pablo Aleza, Valencia (ES); José Cuenca, Valencia (ES); José Manuel Julve, Valencia (ES); José Antonio Pina, Valencia (ES)

(73) Assignee: Instituto Valenciano De Investigaciones Agrarias (IVIA), Valencia (ES)

( * ) Notice: Subject to any disclaimer, the term of this patent is extended or adjusted under 35 U.S.C. 154(b) by 0 days.

(21) Appl. No.: 12/457,675

(22) Filed: Jun. 18, 2009

(65) Prior Publication Data

US 2010/0017926 P1 Jan. 21, 2010

(30) Foreign Application Priority Data

Jul. 21, 2008 (EP) ..... 20081610

(51) Int. Cl.
*A01H 5/00* (2006.01)

(52) U.S. Cl. ..... Plt./202

(58) Field of Classification Search ..... Plt./201, Plt./202

See application file for complete search history.

*Primary Examiner*—Susan B McCormick Ewoldt
(74) *Attorney, Agent, or Firm*—Buchanan Ingersoll & Rooney PC

(57) ABSTRACT

A new and distinct triploid *Citrus hybrida* cultivar is provided that is the product of controlled cross-pollination of two diploid parental plants. The new cultivar forms attractive obloid-shaped late-maturing substantially seedless fruit having an excellent mildly acidic flavor and a pleasant aroma. The leaves are dark green in coloration. The growth habit is vigorous and drooping.

2 Drawing Sheets

Figure 1:
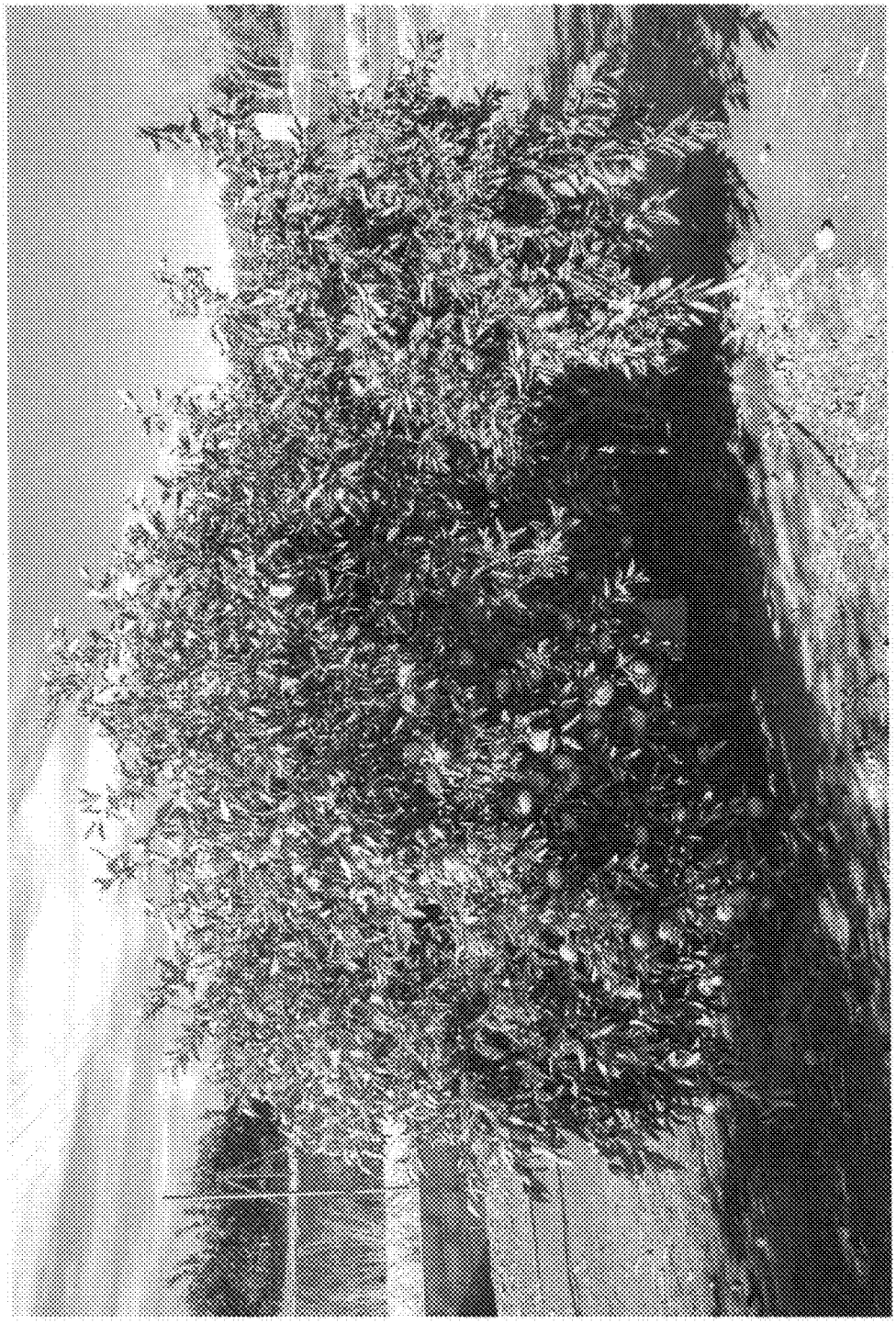

Botanical/commercial classification: *Citrus hybrida*/Mandarin Orange Tree.

Varietal denomination: cv. Garbi.

BACKGROUND OF THE INVENTION

*Citrus* crops including Mandarin Oranges are recognized to be important to the agricultural economy in many parts of the world.

The new hybrid *Citrus* cultivar of the present invention was created during the spring of 1996 at Moncada, Valencia, Spain, when two parents were crossed which previously had been studied in the hope that they would contribute the desired characteristics required to produce quality late-ripening seedless fruit. The female parent (i.e., the seed parent) was the 'Fortune' Mandarin cultivar (non-patented in the United States). 'Fortune' is recognized to be a diploid formed by the hybridization of *C. clementina*×*C. tangerina*. The male parent (i.e., the pollen parent) was the 'Murcott' tangor cultivar (non-patented in the United States). 'Murcott' is a diploid of *C. reticulata*×*C. sinensis*. In order to achieve the cross, the anthers of the 'Murcott' tangor cultivar were removed from flowers collected during pre-anthesis and were dried in Petri dishes over silica gel in a desiccator. Dried dehisced anthers were stored in small Petri dishes at −20° C. The controlled cross-pollination was carried out by applying one anther from the male parental plant to a receptive stigma of a flower of the female parental plant. Approximately 100 flowers of the female parental plant were pollinated. From these female parental plants, 45 fruits were collected that contained 129 small seeds. Embryos numbering 122 were isolated from these seeds and were cultured in vitro. Small plants numbering 116 were recovered and were maintained. When analyzed by the use of flow cytometry, each of the small plants was confirmed to be a triploid. The resulting plants were transferred to standard potting mix and were grown under greenhouse conditions until September, 1998. Each plant next was grafted on 'Carrizo' Citrange rootstock (non-patented in the United States), which is recognized to be a cross of *C. sinensis*×*Poncinus trifoliate,* and was planted in the field for detailed evaluation. These plants first flowered during the spring of 2002, and a single plant of the present invention was selected during 2004, and was further grafted (as described) for further evaluation. The new plant initially was designated IVIA TRI 1.

It was found that the new triploid Mandarin Orange hybrid plant of the present invention displays the following combination of characteristics:

(a) displays a vigorous and drooping growth habit,
(b) forms dark green leaves, and
(c) forms attractive substantially homogeneous easy-to-peel obloid-shaped late-maturing fruit having a large diameter which is substantially seedless with an excellent mildly acidic flavor and a pleasant aroma.

The new cultivar readily can be distinguished from its parental cultivars. More specifically, each parent plant is a diploid, unlike the triploid character of the new cultivar of the present invention.

The new cultivar also can be readily distinguished from the 'Safor' cultivar (U.S. Plant patent application Ser. No. 12/457,676, filed concurrently herewith). The 'Safor' cultivar displays a more erect drooping growth habit and forms fruit of medium-late maturity whereas the present cultivar forms fruit of late maturity.

The asexual reproduction of the new cultivar of the present invention by grafting on 'Carrizo' rootstock at Moncada, Valencia, Spain, has confirmed that the combination of characteristics is stable and is strictly transmissible by such asexual propagation from one generation to another. Accordingly, the new cultivar of the present invention undergoes asexual propagation in a true-to-type manner.

The new plant of the present invention has been named 'Garbi'.

BRIEF DESCRIPTION OF THE PHOTOGRAPHS

The accompanying photographs show as nearly true as it is reasonably possible to make in color illustrations of this character, typical specimens of the new cultivar. The plant was grown at Moncada, Valencia, Spain, and was grafted on 'Carrizo' rootstock.

FIG. 1 illustrates a typical tree on Jan. 7, 2008 at an age of approximately three years and six months. The drooping growth habit is illustrated.

Figure 2:
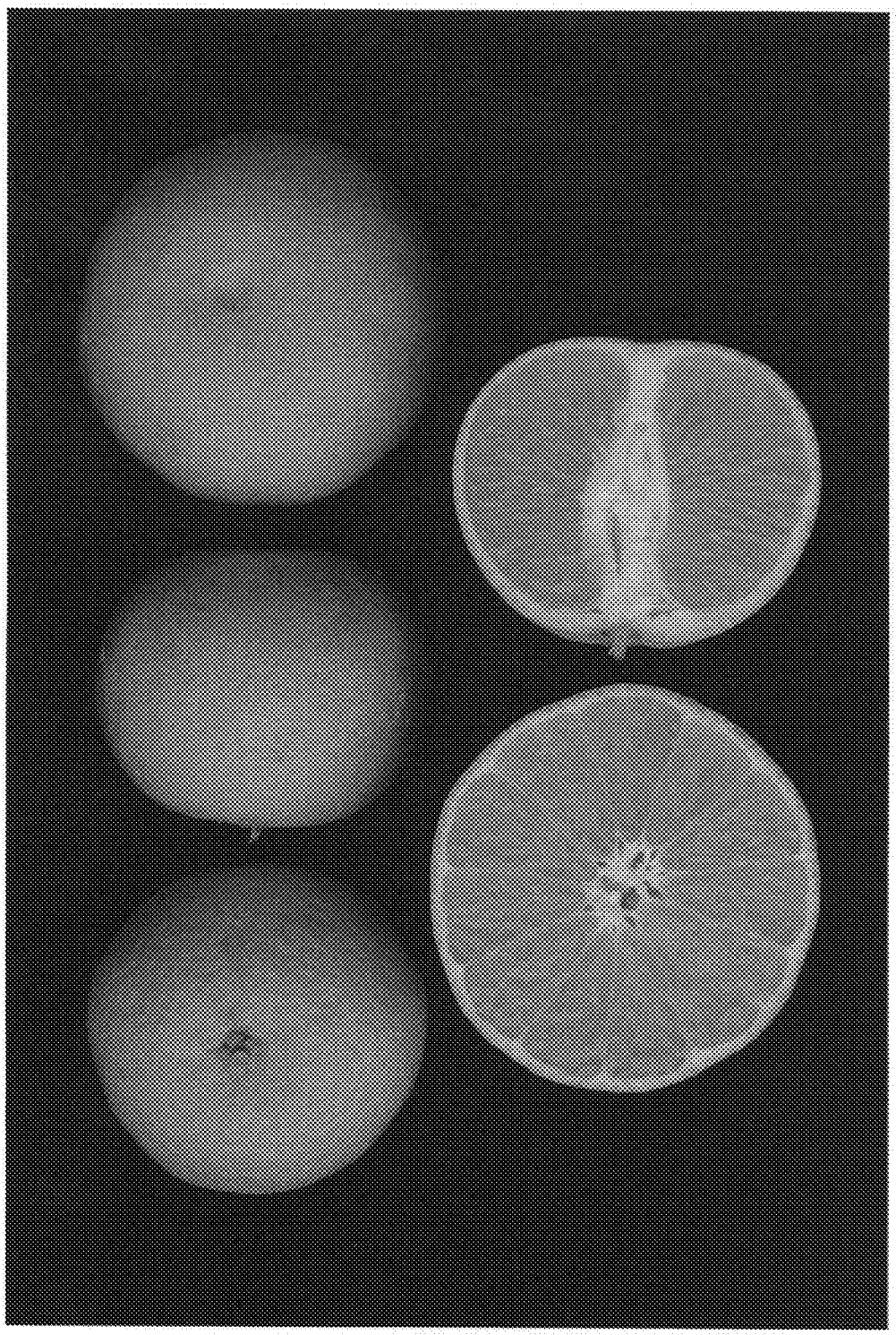

FIG. 2 illustrates typical attractive fruit on Feb. 28, 2007. The fruit flesh is shown in cross-section at the bottom and external views of the fruit are shown at the top. The substantially uniform and homogeneous appearance of the fruit is illustrated.

DETAILED DESCRIPTION

The description is based on the observation of plant of the new cultivar while grafted on 'Carrizo' rootstock and growing outdoors at Moncada, Valencia, Spain. The chart used in the identification of colors is that of The Royal Horticultural Society (R.H.S. Colour Chart), London, England. Common color terms are to be accorded their customary dictionary significance.

Classification: *Citrus hybrida.*

Tree:

- *Ploidy.*—Triploid.
- *Growth habit.*—Vigorous, drooping, and commonly obloid-shaped.
- *Height.*—Commonly approximately 2.8 m on average at an age of five years.
- *Width.*—Commonly approximately 2.1 m on average at an age of five years.
- *Trunk diameter.*—Commonly approximately 7 cm on average at an age of five years measured 40 cm above the ground.
- *Bark.*—Green Group 137A in coloration when young.
- *Bark strength.*—Somewhat fragile.
- *Thorns.*—Dense and long, approximately 30 mm in length on main branches, and new branches commonly bear thorns near approximately 80 percent of the buds having lengths of approximately 7.2 mm on average.

Leaves:

- *Bearing.*—Evergreen.
- *Size.*—Commonly approximately 11.5 cm in length on average, and approximately 3.8 cm in width on average at the widest point.
- *Configuration.*—Somewhat oblong.
- *Apex.*—Acute.
- *Margins.*—Crenate.
- *Petiole.*—Commonly approximately 13.6 mm in length on average with small wings.
- *Color.*—Dark green, Green Group 139A on the upper surface, and lighter green, Green Group 137C on the under surface.

Inflorescence:

- *Time.*—Commonly during April at Moncada, Valencia, Spain.
- *Type.*—Solitary in a raceme arrangement at axillary and terminal positions.
- *Width.*—Approximately 3.6±0.6 cm on average.
- *Petals.*—Five in number, approximately 12.3±0.5 mm in length on average, and approximately 5.5 mm in width on average.
- *Color.*—White, White Group 155C.
- *Stamen.*—Common approximately 20 to 23 in number on average, arranged separately and free, approximately 6.5±0.7 mm in size, and white in color.
- *Pollen.*—Largely sterile with about 0.4 percent of the pollen grains being capable of germinating using in vitro culture during observations to date when compared to more than 82 percent for the female parent 'Fortune' Mandarin cultivar.
- *Pistil.*—One in number, the ovary is generally ellipsold in shape, approximately 2.7 mm in diameter on average, and green in coloration.
- *Style.*—Similar to that of the 'Fortune' and 'Murcott' parental cultivars.
- *Stigma.*—Similar to that of the 'Fortune' and 'Murcott' parental cultivars.

Fruit:

- *Time of maturity.*—Late, commonly mid-February to the end of April at Moncada, Valencia, Spain.
- *Size.*—Commonly 58 mm in height on average, and approximately 65 to 70 mm (i.e., approximately 69 mm on average) in diameter.
- *Weight.*—Commonly approximately 63±21 g on average.
- *Configuration.*—Obloid, circular in shape in transverse section, broadest part of the middle, absent a neck, generally the shape at the proximal end is slightly rounded, with general absence of any substantial depression at stalk end, with absence of or with few radial grooves at the stalk end, with absence of radial grooves at distal end, with absence of a collar, and somewhat flattened at distal end with the presence of a slight depression.
- *Stylar scar.*—Medium in diameter, and with no persistence of style.
- *External color.*—Medium orange, near Orange Group 25A. The coloration is similar to that of 'Clemenules' Clementine (non-patented in the United States).
- *Surface texture.*—Generally smooth with strong glossiness.
- *Oil glands.*—More or less uniform in size with absence of pitting and pebbling and with a pleasant aroma.
- *Internal flesh coloration.*—Near Orange Group 25A.
- *Rind.*—Thin, easy-to-peel, commonly approximately 2.8 mm in thickness on average, with medium adherence to the flesh, medium in strength, and medium in oiliness.
- *Core.*—Commonly approximately 12.6±0.9 mm in diameter on average.
- *Flesh segments.*—Medium in number, commonly approximately 10 or 11 well-developed segments per fruit, with medium coherence of adjacent wall segments, with elongated juice vesicles, and with medium thickness of juice vesicles. The typical size of such segments is illustrated at the lower portion of FIG. 2.
- *Navel.*—Absent or very rare.
- *Parthenocarpy.*—Seedless fruit typically is formed, or with very few seeds on rare occasions.

*Eating quality.*—Texture of segments renders the fruit easy to eat with the presence of a high quality juice and a pleasant aroma.

*Juice content.*—Commonly approximately 48 percent at maturity.

*Acidity.*—Lightly acidic, with approximately 1.8 percent acid concentration at maturity, and with near 18° Brix.

*Pulp texture.*—Firm.

*Fruit productivity.*—Similar to that of the parental 'Fortune' and 'Murcott' cultivars.

Development:

*Resistance to diseases.*—During observations to date is tolerant to *Citrus Tristeza Virus* (*CTV*) and *Alternaria* spp.

*Resistance to pests.*—Is susceptible to aphids, mites, and scales that commonly are present with Mandarin Orange trees.

*Winter hardiness.*—Similar to that of the parental 'Fortune' and 'Murcott' cultivars.

*Resistance to heat.*—Similar to that of the parental 'Fortune' and 'Murcott' cultivars.

The new 'Garbi' cultivar has not been observed under all possible environmental conditions to date. Accordingly, it is possible that the phenotypic expression may vary somewhat with changes in light intensity and duration, cultural practices, and other environmental conditions.

We claim:

1. A triploid Mandarin Orange hybrid plant having the following combination of characteristics:

(a) displays a vigorous and drooping growth habit, (b) forms dark green leaves, and (c) forms attractive substantially homogeneous easy-to-peel obloid-shaped late-maturing fruit having a large diameter which is substantially seedless with an excellent mildly acidic flavor and a pleasant aroma;

substantially as herein shown and described.

* * * * *